United States Patent
Sharma et al.

(10) Patent No.: US 10,176,896 B2
(45) Date of Patent: *Jan. 8, 2019

(54) CORONARY COMPUTED TOMOGRAPHY CLINICAL DECISION SUPPORT SYSTEM

(71) Applicant: Siemens Healthcare GmbH, Erlangen (DE)

(72) Inventors: Puneet Sharma, Monmouth Junction, NJ (US); Lucian Mihai Itu, Brasov (RO); Thomas Flohr, Uehlfeld (DE); Dorin Comaniciu, Monmouth Junction, NJ (US)

(73) Assignee: Siemens Healthcare GmbH, Erlangen (DE)

(*) Notice: Subject to any disclaimer, the term of this patent is extended or adjusted under 35 U.S.C. 154(b) by 29 days.

This patent is subject to a terminal disclaimer.

(21) Appl. No.: 15/691,855

(22) Filed: Aug. 31, 2017

(65) Prior Publication Data

US 2018/0253531 A1 Sep. 6, 2018

Related U.S. Application Data

(60) Provisional application No. 62/467,269, filed on Mar. 6, 2017, provisional application No. 62/465,198, filed on Mar. 1, 2017.

(51) Int. Cl.
*G16H 50/20* (2018.01)
*G06F 19/00* (2018.01)
(Continued)

(52) U.S. Cl.
CPC ......... *G16H 50/20* (2018.01); *A61B 6/032* (2013.01); *A61B 6/463* (2013.01); *A61B 6/469* (2013.01);
(Continued)

(58) Field of Classification Search
USPC ................................................ 382/128, 131
See application file for complete search history.

(56) References Cited

U.S. PATENT DOCUMENTS 7,693,315 B2 * 4/2010 Krishnan ............. G06T 7/0012
382/100
7,912,528 B2 * 3/2011 Krishnan ............... G16H 50/20
600/407

(Continued)

OTHER PUBLICATIONS

Coenen, Adriaan, et al. "Fractional flow reserve computed from noninvasive CT angiography data: diagnostic performance of an on-site clinician-operated computational fluid dynamics algorithm." Radiology 274.3 (2014): 674-683.

(Continued)

*Primary Examiner* — Ishrat I Sherali

(57) ABSTRACT

A CT-based clinical decision support system provides coronary decision support. With or without CT-FFR, a machine learnt predictor predicts the clinical decision for the patient based on input from various sources. Using the machine learnt predictor provides more consistent and comprehensive consideration of the available information. The clinical decision support may be provided prior to review of coronary CT data by a radiologist and/or treating physician, providing a starting point or recommendation that may be used by the radiologist and/or treating physician.

17 Claims, 3 Drawing Sheets

(51) Int. Cl.
  G06N 99/00 (2010.01)
  G16H 50/50 (2018.01)
  G16H 10/60 (2018.01)
  A61B 6/03 (2006.01)
  A61B 6/00 (2006.01)
  G06K 9/46 (2006.01)
  G06N 5/04 (2006.01)
  G06T 7/00 (2017.01)
  G06K 9/62 (2006.01)

(52) U.S. Cl.
  CPC ............ *A61B 6/507* (2013.01); *A61B 6/5217* (2013.01); *G06F 19/321* (2013.01); *G06K 9/46* (2013.01); *G06K 9/6282* (2013.01); *G06N 5/045* (2013.01); *G06N 99/005* (2013.01); *G06T 7/0012* (2013.01); *G16H 10/60* (2018.01); *G16H 50/50* (2018.01); G06K 2209/051 (2013.01); G06K 2209/27 (2013.01); G06T 2207/10081 (2013.01); G06T 2207/30048 (2013.01); G06T 2211/404 (2013.01)

(56) References Cited

U.S. PATENT DOCUMENTS

| | | | |
|---|---|---|---|
| 9,349,178 | B1 | 5/2016 | Itu et al. |
| 9,538,925 | B2* | 1/2017 | Sharma ............... A61B 5/0261 |
| 9,589,349 | B2* | 3/2017 | Grady ............... G06F 17/30268 |
| 9,974,453 | B2* | 5/2018 | Fonte ............... A61B 6/504 |
| 2005/0020903 | A1* | 1/2005 | Krishnan ............... G16H 50/20 600/407 |
| 2010/0222646 | A1 | 9/2010 | Rao et al. |
| 2018/0249978 | A1* | 9/2018 | Itu ............... G16H 10/60 |

OTHER PUBLICATIONS

Cookson, A. N., et al. "A novel porous mechanical framework for modelling the interaction between coronary perfusion and myocardial mechanics." Journal of biomechanics 45.5 (2012): 850-855.

Itu, Lucian, et al. "A machine-learning approach for computation of fractional flow reserve from coronary computed tomography." Journal of Applied Physiology 121.1 (2016): 42-52.

Koo, Bon-Kwon, et al. "Diagnosis of ischemia-causing coronary stenoses by noninvasive fractional flow reserve computed from coronary computed tomographic angiograms: results from the prospective multicenter Discover-Flow (Diagnosis of Ischemia-Causing Stenoses Obtained Via Noninvasive Fractional Flow Reserve) study." Journal of the American College of Cardiology 58.19 (2011): 1989-1997.

Marwick, Thomas H., et al. "Finding the gatekeeper to the cardiac catheterization laboratory: coronary CT angiography or stress testing?." Journal of the American College of Cardiology 65.25 (2015): 2747-2756.

Min, James K., et al. "Diagnostic accuracy of fractional flow reserve from anatomic CT angiography." Jama 308.12 (2012): 1237-1245.

Nørgaard, Bjarne L., et al. "Diagnostic performance of noninvasive fractional flow reserve derived from coronary computed tomography angiography in suspected coronary artery disease: the NXT trial (Analysis of Coronary Blood Flow Using CT Angiography: Next Steps)." Journal of the American College of Cardiology 63.12 (2014): 1145-1155.

Patel, Manesh R., et al. "Low diagnostic yield of elective coronary angiography." New England Journal of Medicine 362.10 (2010): 886-895.

Patel, Manesh R., et al. "Prevalence and predictors of nonobstructive coronary artery disease identified with coronary angiography in contemporary clinical practice." American heart journal 167.6 (2014): 846-852.

Petraco, Ricardo, et al. "Hybrid iFR-FFR decision-making strategy: implications for enhancing universal adoption of physiology-guided coronary revascularization." American Journal of Cardiology 111.7 (2013).

Renker, Matthias, et al. "Comparison of diagnostic value of a novel noninvasive coronary computed tomography angiography method versus standard coronary angiography for assessing fractional flow reserve." The American Journal of cardiology 114.9 (2014): 1303-1308.

Talo, Richard AP, et al. "Diagnostic Accuracy of Stress Myocardial Perfusion Imaging Compared to Invasive Coronary Angiography With Fractional Flow Reserve Meta-Analysis"; Clinical Perspective; Circulation: Cardiovascular Imaging 8.1 (2015).

* cited by examiner

CORONARY COMPUTED TOMOGRAPHY CLINICAL DECISION SUPPORT SYSTEM

RELATED APPLICATIONS

The present patent document claims the benefit of the filing date under 35 U.S.C. § 119(e) of Provisional U.S. Patent Application Ser. Nos. 62/467,269, filed Mar. 6, 2017, and 62/465,198, filed Mar. 1, 2017, which are hereby incorporated by reference.

BACKGROUND

The present embodiments relate to coronary computed tomography (CT)-based clinical decision support. Clinical decision making based on coronary CT angiography (CCTA) imaging is typically quite subjective. Currently, the decision to send patients to the catheterization laboratory is based on a subjective evaluation of anatomical features on the coronary CT angiography exam. Quantitative tools, such as quantitative lesion grading, total plaque volume, or calcium score, may be used in making this clinical decision. A large amount of other data may be used, but so much information often results in physicians and guidelines focusing on a sub-set of data, the image and a few quantitative tools. However, the current practices have shown low specificity in guiding patients to the catheterization laboratory, with a significant proportion of catheterization laboratory bound patients found to have no ischemia-causing lesions.

In today's clinical practice, the radiologist reports their findings based on a subjective interpretation of the CCTA examination to a treating physician. In certain instances, the radiologist uses some quantitative tools, such as quantitative lesion grading and total plaque volume, for the report. Given that there are multiple physicians involved, there may be delays in deciding upon treatment and less than all available information may be used.

One proposed solution to increase specificity is to use CT-based fractional flow reserve (CT-FFR) to better select patients who need to be referred to the catheterization laboratory. Over the last five years, non-invasive CT-FFR has been clinically validated in a several large studies. Several methods have been proposed for the computation of CT-FFR, namely 3D Computational Fluid Dynamics (3D CFD), hybrid reduced order CFD, lumped modeling, and machine learning (ML-FFR). Each of these methods have yielded very similar diagnostic performance in terms of sensitivity, specificity, positive and negative predictive value in well controlled prospective or retrospective clinical trials and clinical studies. In all these trials, a cut-off value of 0.8 is used for objective evaluation of the CT-FFR results against invasive FFR.

Due to the relatively low specificity of CT imaging, patients with intermediate lesions might be evaluated using CT-FFR. However, CT-FFR is expensive, and is currently not commonly utilized. The computation of CT-FFR typically requires a segmented anatomical model of the coronary anatomy, which is time consuming. Further, the computation of CT-FFR itself requires considerable computational effort. As a result, although CT-FFR is currently the most promising candidate for acting as a gatekeeper to the cardiac catheterization laboratory, the clinical utility of CT-FFR is hampered both by the time required to process one case as well as the cost of computing CT-FFR. Given the scarcity of use, there is no well-defined integration of CT-FFR for clinical decision making, especially since the head-to-head diagnostic accuracy against invasive FFR is moderate. Decision making based on coronary CT image interpretation and CT-FFR number may remain primarily subjective in nature.

SUMMARY

By way of introduction, the preferred embodiments described below include methods, systems, instructions, and non-transitory computer readable media for coronary decision support using a CT-based clinical decision support system. With or without CT-FFR, a machine learnt predictor predicts the clinical decision for the patient based on input from various sources. Using the machine learnt predictor provides more consistent and comprehensive consideration of the available information. The clinical decision support may be provided prior to review of coronary CT data by a radiologist and/or treating physician, providing a starting point or recommendation that may be used by the radiologist and/or treating physician.

In a first aspect, a method is provided for coronary decision support using a computed tomography (CT)-based clinical decision support system. A CT system scans a patient, providing coronary CT data representing a heart of the patient. Patient data different than the coronary CT data is acquired from a computerized medical record database. Values for features of an input vector of a machine-learnt predictor of the CT-based clinical decision support system are extracted from the coronary CT data and the patient data. The machine-learnt predictor of the CT-based clinical decision support system generates a clinical decision for treatment of the patient based on the input vector. The clinical decision is transmitted.

In a second aspect, a system is provided for coronary decision support. A computed tomography (CT) scanner for scanning a patient is configured to output coronary CT data for the patient. A memory stores a computerized patient record. A decision support processor is configured to extract an input feature vector from the coronary CT data and the computerized patient record, to apply the input feature vector to a machine-learnt classifier, and to output a clinical decision for the patient from the machine-learnt classifier in response to the application of the input feature vector.

In a third aspect, a method is provided for coronary decision support using a clinical decision support system. Coronary computed tomography (CCT) scan data for a patient and other non-invasive patient data for the patient to a machine-learnt clinical decision support system. The machine-learnt clinical decision support system generates, in response to the input, a clinical decision for the patient. The clinical decision is transmitted as a recommendation for treatment of the patient.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

For coronary CT-based clinical decision support, a machine learning (ML) algorithm trains for predicting clinical decisions after coronary CT exams. For example, the machine-trained predicator outputs whether to: send the patient to the catheterization laboratory for further invasive testing and/or intervention (e.g. diagnostic catheterization, percutaneous coronary intervention (PCI), or coronary artery bypass grafting (CABG), send the patient for another non-invasive testing (e.g., perfusion imaging, single photon emission computed tomography (SPECT), or stress echocardiography), discharge the patient, or prescribe medication. The prediction is based on one or more measurements extracted from non-invasive patient data, medical imaging data, blood, serum biomarkers, genomics, demographics, patient history, and/or information regarding anatomical or functional evaluation of arteries from other models. The proposed machine learning-based workflow integrates data from heterogeneous sources to perform a comprehensive assessment. The online prediction phase is extremely fast, outputting results in near real-time, and may be run directly on a workstation on-site.

For training the machine learnt predictor, a large database of patient data containing clinical decisions with or without patient outcome data is used. Once trained, coronary CT imaging data alongside other medical data of the patient (e.g., demographics and blood biomarkers) is used to extract features. The features are input to the machine-learnt predictor to predict clinical decisions after the coronary CT examination. An offline trained machine learning algorithm is used to predict the decisions related to coronary artery disease.

In one embodiment, the clinical decision is whether to perform CT-FFR. By using various data, such as the coronary CT-data, the predicator may recommend CT-FFR for appropriate cases, but avoid CT-FFR for other cases. This second opinion information may be provided for consideration by a physician for a specific patient, incorporating CT-FFR in the decision process in a way not currently used.

Figure 1:
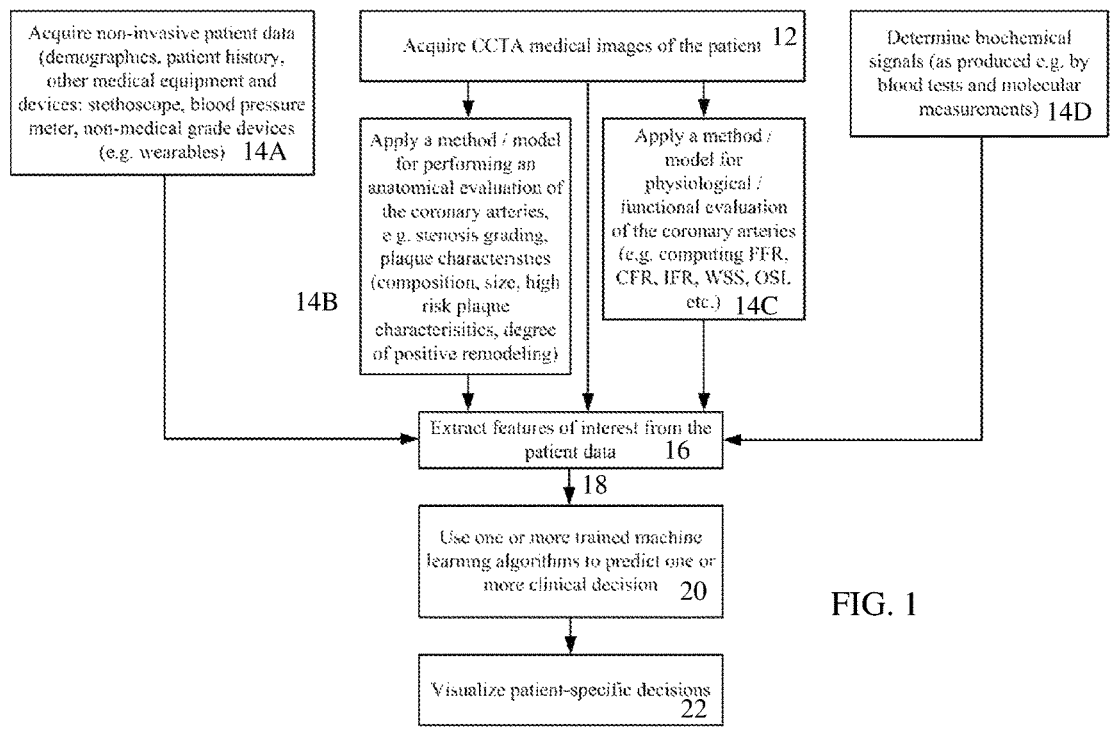
FIG. 1 is a flow chart diagram of one embodiment of a method for coronary CT-based clinical decision support.

FIG. 1 is a flow chart of one embodiment of a method for coronary decision support using a computed tomography (CT)-based clinical decision support system. Clinical decision support is based on non-invasive coronary computed tomography angiography (CCTA) data. A machine learning algorithm is trained to predict the clinical decision for a given patient instead of predicting a surrogate metric, such as stenosis grade, CT-FFR, or risk of plaque rupture.

The flow chart represents a generic workflow to be used for predicting the clinical decision after a CCTA exam. The acts of the method are performed upon completion of scanning and before a review by a treating physician and possibly before review by a radiologist. The method may be applied at the time of any type of medical imaging or non-imaging exam for clinical decision support in the context of cardiovascular disease. The method may be used at other times, such as activated by the treating physician during review by that physician.

In a specific example, the CT-based clinical decision support system provides fractional flow reserve (FFR) decision support. The decision support system outputs a recommendation to run/not run CT-FFR or other functional testing. A patient-specific indication of non-invasive FFR assessment is provided. The current clinical workflows, including those where CT-FFR is computed, do not completely utilize the rich information in the images and measurements from the patient. In this context, the decision support system is a gatekeeper for the CT-FFR test. For patient-specific conditions, the support system indicates if the CT-FFR test would provide useful incremental information in the clinical decision-making process. The machine-learnt predictor is trained to predict the incremental utility of performing CT-FFR (i.e., to identify patients where the likelihood of either a positive or negative CT-FFR test may be predicted using image features with high confidence and without directly computing CT-FFR). In this subset of cases, the patient may be either directed to the catheterization laboratory or to medical therapy without the time and cost associated with CT-FFR. In the remaining cases, CT-FFR or other functional testing may be recommended.

The acts are performed in the order shown (e.g., top to bottom or numerical) or other orders. For example, acts 12 and 14 are performed in any order. As another example, acts 12, 14, and 16 may be performed repetitively in a series of sequences.

Additional, different, or fewer acts may be provided. For example, the method is performed without one, two, or all of acts 14A-D. In another example, act 22 is not performed. As another example, acts for configuring a medical scanner are provided.

Figure 5:
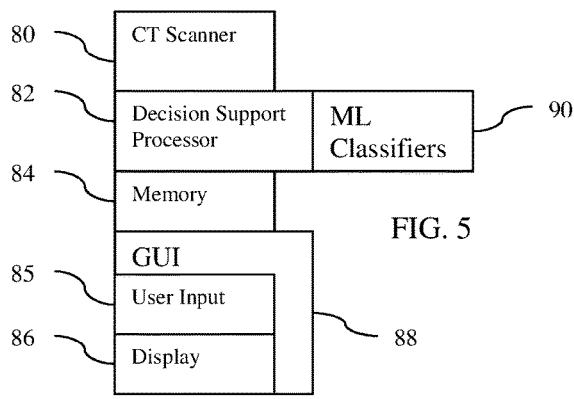
FIG. 5 is one embodiment of a system for coronary CT-based clinical decision support.

The acts are performed by the system of FIG. 5 or another system. For example, act 12 is performed by CT scanner. Acts 14A-D are performed by a decision support processor interacting with a user interface and/or a memory. Acts 16-22 are performed by the decision support processor. In one example, the CT scanner performs all the acts. In yet another example, a workstation, computer, portable or handheld device (e.g., tablet or smart phone), server, or combinations thereof performs one or more of the acts. A workstation or CT scanner may be used as a gatekeeper for CT-FFR decisions and/or whether to have CT-FFR performed offsite or by a service.

In act 12, one or more medical images or datasets are acquired. The medical image is a frame of data representing the patient. The data may be in any format. While the terms "image" and "imaging" are used, the image or imaging data may be in a format prior to actual display of the image. For example, the medical image may be a plurality of scalar values representing different locations in a Cartesian or polar coordinate format different than a display format (i.e., scan or voxel data). As another example, the medical image may be a plurality red, green, blue (e.g., RGB) values output to a display for generating the image in the display format. The medical image may not yet be a displayed image, may be a currently displayed image, or may be previously displayed image in the display or other format. The image or imaging is a dataset that may be used for anatomical imaging, such as scan data representing spatial distribution of anatomy (e.g., coronary arteries) of the patient.

The medical image is obtained by loading from memory and/or transfer via a computer network. For example, previously acquired scan data is accessed from a memory or database. As another example, scan data is transmitted over a network after acquisition from scanning a patient. In other embodiments, the medical image or scan data is obtained by scanning the patient.

Any type of medical image may be used. In one embodiment, a CT scanner or system acquires CT scan data representing a patient. CT scan data is acquired by rotating a source of x-rays and an opposing detector about a patient. Any range and/or path of travel may be used, such as rotating along a helical path of travel. C-arm or other x-ray imaging may be used instead. Computed tomography is then used to determine the two or three-dimensional distribution of x-ray attenuation from the projections detected by the detector. In other embodiments, other types of scan data or medical images are obtained, such as magnetic resonance, x-ray, ultrasound, positron emission tomography (PET), single photon emission computed tomography (SPECT), or other medical imaging modality.

Coronary CT angiography is performed to acquire the coronary CT data representing a heart or coronary region of the patient. Other coronary CT data may be acquired, such as Dual Energy or Photon Counting data. The coronary CT data is acquired for a stable or acute patient being examined for coronary artery disease.

Based on the received detected intensities, a three-dimensional representation of the patient (i.e., the density or absorption as a function of voxel or location) is generated by computed tomography processing. Alternatively, the scan data represents a two-dimensional cross-section of the patient. Data representing an interior region of a patient is obtained. The frame of data represents a two or three-dimensional region of the patient. Values are provided for each of multiple locations distributed in two or three dimensions.

In acts 14A-D, patient data different than the coronary CT data is acquired. The decision support processor or other processor acquires the patient data from a computerized medical record database or other memory. The stored information for a specific patient is accessed by look-up, mining, searching, and/or receipt over a network.

The types of data acquired are separated into four categories corresponding to acts 14A-D, but other categorizations may be used. Patient data from one, two, three, all four, or none of the categories may be acquired. Act 14A corresponds to acquiring non-invasive clinical data. Act 14B corresponds to acquiring patient data for anatomy derived from coronary CT and/or other imaging data. Act 14C corresponds to acquiring patient data for functional or physiological operation derived from the coronary CT and/or other imaging data. Act 14D corresponds to acquiring patient data for biochemical measurements.

Acts 14B and 14C may fit models, such as anatomical model, functional model, or physiological model to the scan data. In one embodiment, values for CT-FFR at different locations in the patient are acquired using 3D CFD, hybrid reduced order CFD, lumped modeling, or ML-FFR. By acquiring CT-FFR, invasive measurements of FFR may be avoided or put off. Invasive FFR is not performed prior to generating a recommendation by the clinical decision support system.

The output of any type of machine learnt, physics, or physiological model using coronary CT or other medical imaging data may be used. For example, a cascaded workflow uses the model to derive anatomical and/or functional information, which is then used for decision support. Example outputs from modeling include physiological or functional evaluation of the coronary arteries: computed FFR (cFFR), coronary flow reserve (CFR), instantaneous wave-free ratio (IFR), wall shear stress (WSS), and/or oscillatory shear index (OSI) at one or more locations of the coronary arterial tree. Example outputs of a model performing an anatomical evaluation of the coronary arteries include: stenosis grade, stenosis length, stenosis location, and/or plaque characteristics (e.g., composition, size, high risk plaque characteristics, and/or degree of positive remodeling). Other metrics may be derived from the coronary CT data, such as image quality, calcium score, transluminal contrast attenuation gradient (TAG), and/or risk scores (e.g., segment stenosis score, segment involvement score, and/or Framingham risk score).

In one embodiment, FFR is computed for all or multiple locations in a mesh fit to the coronary arterial tree as represented by the coronary CT data. Additional features may be extracted from these results, such as: type of disease (e.g., diffuse disease or focal disease (e.g., by inspecting for example a virtual pull back curve from the terminal segments of the anatomical model to the ostium)), the number of functionally significant lesions (e.g., serial lesions), and/or prevalence of coronary artery disease (e.g., the number of main and/or side branches being effected). Where the model may be used for uncertainty quantification for the physiological measures, the uncertainty or confidence intervals computed with such methods may be employed as additional features or acquired data. Another important type of feature is the myocardial territory supplied by each coronary artery. The territory associated to each coronary artery may be determined, such as by perfusion modeling. In alternative embodiments, CT-FFR is not computed prior to generating a clinical decision.

Besides the coronary CT data, input information for making a clinical decision may be extracted from one or more of many sources. Other medical equipment and devices, such as a stethoscope, blood pressure meter, and/or laboratory diagnostics (e.g., blood pressure, heart rate, ECG signals), may be used to provide patient data. Other example data include any one or more of: the type of patient (e.g., stable or acute), patient eligibility for certain types of tests (e.g., the patient may not be eligible for tests based on physical exercise), the availability of certain tests or scanners (e.g., some medical devices may be unavailable at a facility or unavailable at certain time points due to maintenance), cost of a test or treatment (e.g., depending on the type of insurance of the patient only some tests may be covered by the insurance), pre-test probability (PTP) of coronary artery disease (CAD) (e.g., Farmington risk or clinical likelihood that spontaneous coronary artery dissection (SCAD) is present based on clinical characteristics such as chest pain classification, age, and gender), results of previously performed non-invasive stress tests (e.g., Myocardial Perfusion Imaging (MPI), Multigated Acquisition (MUGA) Scan, Radionuclide Stress Test and Nuclear Stress Test, Exercise Stress Test, Electrocardiogram (EKG/ECG), and/or Stress or rest echocardiography), measurements from non-medical grade devices (e.g. wearables, watches, pedometers, smartphones, and/or tablets), biochemical signals as produced by blood tests and/or molecular measurements (e.g., proteomics, transcriptomics, genomics, metabolomics, lipidomics, and epigenomics), features extracted based on radiogenomics (imaging biomarkers that are linked with the genomics of a pathology), demographic information (e.g., age, ethnicity, gender, weight, height, race, body max index (BMI), diabetes, hypertension, hypercholesterolemia, smoking history, family history of CAD, prior myocardial infarction (MI), prior PCI, prior CABG, and/or angina type (e.g., stable/worsening/silent ischemia/other angina category, according to CCS, AHA/ACC)), clinical history of the patient (e.g., the patient may have been exposed to radiation recently due to other medical exams), and/or genetic, radiogenomic or other phenotype based features of the patient.

Any sub-set or all these different types of information may be acquired at a single time point or at different time points. For example, features extracted from a previous coronary CT angiography or from an angiographic exam may be used to predict one or more measures of interest. Similarly, blood biomarkers (the same or different) may be acquired at different time points and used as features. The same type of information may be acquired at different times, providing a time series of information. One type of information may be acquired at a same or different time as another type of information.

In act 16, the clinical decision support processor extracts values for features of an input vector of a machine-learnt predictor. A sub-set of the acquired data from acts 12 and 14A-D is selected. Alternatively, acts 12 and 14A-D are only performed for the features of the input vector, so acquisition may be extraction. The machine-learnt or other predictor uses a given set of features. Patient data available for those features is used to determine the value of the features.

The extraction is from the coronary CT data and the patient data. For example, the CT-FFR value, clinical data, values from the modeling or model fit to the CT or other imaging data, and/or coronary CT data are used as sources of information for extraction.

The extraction may be selecting or determining the value. For example, the CT-FFR value is selected without change for the input vector. As another example, anatomical, functional, measured, or other values of acquired patient data are used as values for the input vector. Alternatively, the extraction alters the acquired values, such as by filtering or combining information.

For the coronary CT data, the extraction calculates representative information from the CT data. For example, Haar wavelets, steerable, and/or other filter kernels are applied to the CT data to calculate the values of features. In another example, a deep learnt kernel for a feature is convoluted with the CT data to determine the values of the feature spatially across the CT data. Alternatively, the intensities or scalar values of the coronary CT data are used as values of the input vector.

Different predictors may use different input vectors. Different sets of values may be extracted for different predictors. Alternatively, one set is extracted for all predictors or only one predictor.

In the embodiment for deciding whether to apply CT-FFR, the only features may be directly derived from the coronary CT data. Rather than modeling, convolution is used to determine the values of the features. Alternatively, values are extracted from the CT data, non-invasive patient data (e.g., clinical data), modeling data, and/or biochemical measurements.

In act 18, the extracted values are input to the machine-learnt clinical decision support system. The input is by applying the values to the matrices representing the machine-learnt predictor. The coronary CT scan data for a patient is input in the form of values for features. Other patient data, such as non-invasive patient data for the patient, may be input in the form of the extracted values. The other data may include clinical data, biochemical measurements, estimates of function from a functional or physiological model fit to the CT data, and/or estimates of anatomy from an anatomical model fit to the CT data.

In act 20, the clinical decision support processor or system generates one or more clinical decisions for treatment of the patient. By applying the values of the input vector to the matrices or variables of the predictor, the clinical decision appropriate for that patient is output as a prediction to support the actual decision to be made by the treating physician.

The clinical decision for the patient is performed prior to review of images from the coronary CT scan data by the treating physician or other physician in charge of treatment decisions for the patient. The generation of the decision may be performed prior to review of images by a radiologist or other to derive measures or indications of health of the patient. Alternatively, the generation occurs at later times, such as on demand.

The predictor is a machine-learnt predictor of the CT-based clinical decision support system. Machine learning uses training data of labeled or ground truth scan to learn to predict the clinical decision. The training data is used as knowledge of past cases to train the classifier to classify the patient into decision groups or options. The training associates the features of the input vector with clinical decisions.

Any machine learning or training may be used. A probabilistic boosting tree, support vector machine, neural network, sparse auto-encoding classifier, Bayesian network, or other now known or later developed machine learning may be used. Any semi-supervised, supervised, or unsupervised learning may be used. Hierarchal or other approaches may be used. In one embodiment, the classification is by a machine-learnt classifier learnt with deep learning. As part of identifying features that distinguish between different outcomes, the classifier is also machine learnt. Any deep learning approach or architecture may be used. For example, a convolutional neural network is used. The network may include convolutional, sub-sampling (e.g., max pooling), fully connected layers, and/or other types of layers. By using convolution, the number of possible features to be tested is limited. The fully connected layers operate to fully connect the features as limited by the convolution layer after maximum pooling. Other features may be added to the fully connected layers, such as non-imaging or clinical information. Any combination of layers may be provided. Hierarchical structures are employed, either for learning features or representation or for classification or regression. The computer-based decision support system employs a machine learning algorithm for automated decision making.

In alternative embodiments, a model other than a machine-learnt predictor is used. Rule based (e.g., decision tree), reduced order (e.g., lumped parameter model of the coronary circulation system), or other models are used. For example, for deciding whether to perform CT-FFR, the size and other characteristics of the anatomy are used heuristically or based on rules to predict this clinical decision. Rule-based or multi-criteria decision making (MCDM) approaches like aggregated indices randomization method (AIRM), analytic hierarchy process (AHP), analytic network process (ANP, an extension of AHP), elimination and choice expressing reality (ELECTRE), measuring attractiveness by a categorical based evaluation technique (MACBETH), multi-attribute global inference of quality (MAGIQ), potentially all pairwise rankings of all possible alternatives (PAPRIKA), preference ranking organization method for enrichment evaluation (PROMETHEE), or the evidential reasoning approach for MCDM under hybrid uncertainty may be used.

The machine-learnt predictor, with or without deep learning, is trained to associate the categorical labels (output clinical decision of what to do next for the patient) to the extracted values of one or more features. The machine-learning uses training data with ground truth to learn to predict based on the input vector. The resulting machine-learnt predictor is a matrix for inputs, weighting, and combination to output a clinical decision. Using the matrix or matrices, the processor inputs the extracted values for features and outputs the prediction.

Figure 2:
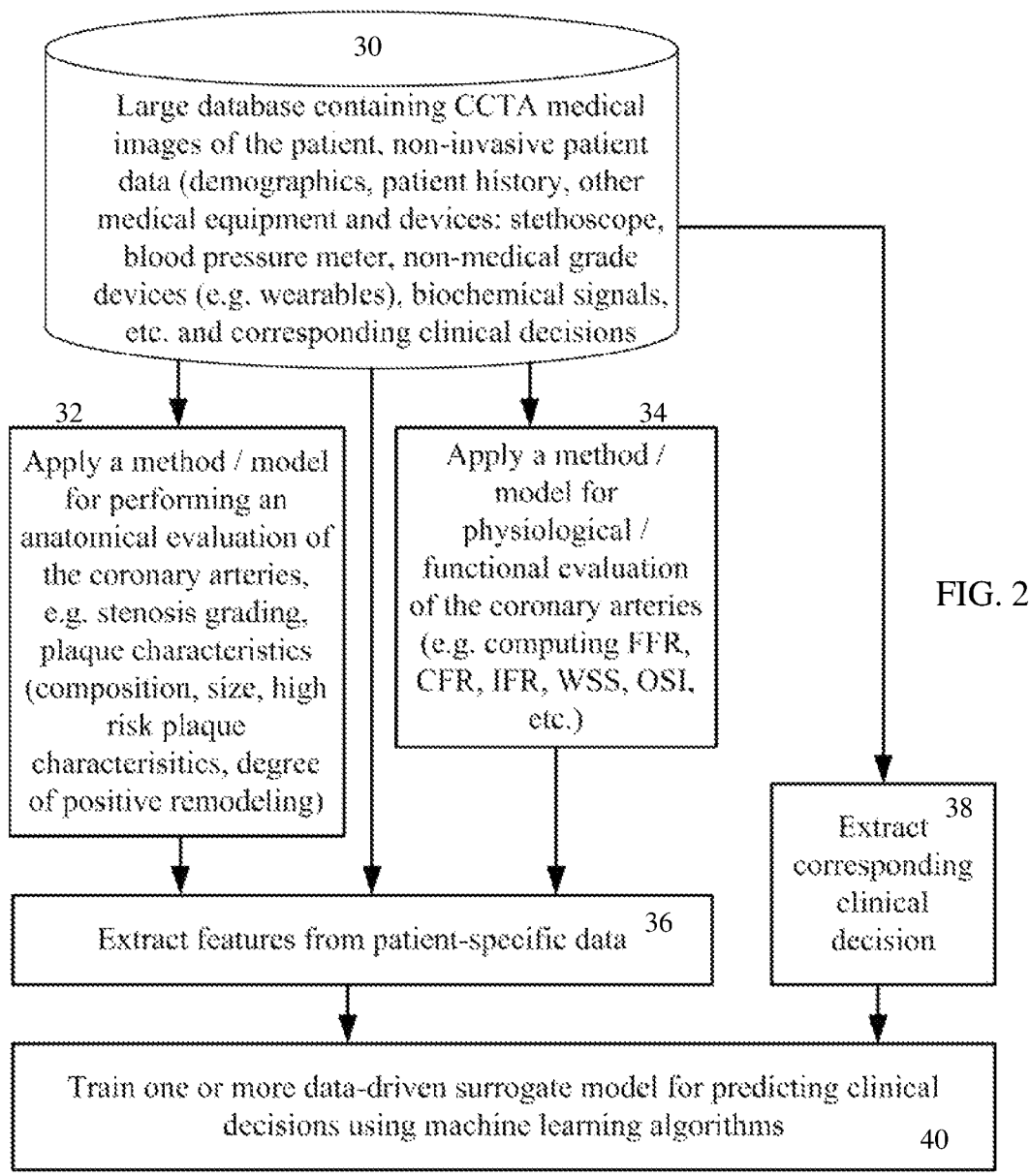
FIG. 2 illustrates an embodiment of machine learning a predictor for coronary CT-based clinical decision support.

FIG. 2 shows one embodiment for training with machine learning. To train, a large database 30 based on patient-specific data is acquired. The database 30 contains numerous pairs of patient data sets (input data—as acquired during trials or collected in registries), and the corresponding decisions that were taken by the clinicians after the coronary CT angiography exam.

Each recorded decision may additionally have a label representing the correctness of the decision. The label may be represented by a binary variable as correct or incorrect or may be represented as a continuous variable representing a range of correctness. The value of this correctness label may be derived from patient outcome (e.g. number of or time of next major adverse cardiac event (MACE), days of hospitalization, date of re-hospitalization, or subsequent clinical exams and their results). The correctness label may already exist when the training database 30 is set up or may be generated based on the patient outcome. Manual or automated methods may be employed for assigning labels to the decision (e.g. machine-learnt classification or rule based model). In alternative embodiments, correctness is not provided.

In one embodiment, only the decisions to which a positive label (correct decision) has been assigned are used for the training. Alternatively, all decisions, both correct and incorrect, may be used for the training. The incorrect decisions are used as penalization samples to discourage the model from taking such a decision in a similar situation.

The database 30 contains patient-specific data, such as the same types of data acquired in acts 12 and 14A-D of FIG. 1. For example, data for many different patients includes: coronary CT data (e.g., angiography medical images or scan data), non-invasive patient data (e.g., demographics and patient history), measures from other medical equipment and devices (e.g., measures from stethoscope, blood pressure meter, non-medical grade devices (e.g. wearables)), and/or biochemical signals. For each patient, the corresponding clinical decisions that were made are included. Data sets for tens, hundreds, thousands, or more patients are acquired.

Data from anatomical modeling and/or functional modeling may be acquired or be part of the database 30, such as where the modeling for the patients was previously fit to the CT data for those patients. Where such model fitting was not performed, the modeling may be applied 32, 34 to the CT data for the patients in the database 30. This provides additional data that may be used for extracting 36 values for features. Other machine-learnt or rule-based methods may be employed to extract additional features relevant for the anatomical and functional evaluation of the coronary arteries, which are in turn important for the clinical decision to be taken.

Some or all the data of the database 30 may be generated synthetically. Rather than using data for an actual patient, data is generated by perturbing patient data to create samples not from an actual patient. A non-patient physical model (e.g., tubes to represent the coronary artery tree with fluid simulating blood and a pump simulating pressure from the heart) may be used. Generic or non-patient specific computer modeling may be used to generate the data. Synthetic images, synthetic anatomical models, and/or other non-patient-specific data may be used.

Since invasively measured FFR is the current gold standard in the functional evaluation of coronary artery disease, the training may be based on a patient-specific database 30 that includes invasively measured FFR or other coronary functional diagnostic indices (e.g., coronary flow reserve (CFR), instantaneous wave-free ratio (IFR), index of microcirculatory resistance (IMR), basal stenosis resistance (BSR), hyperaemic stenosis resistance (HSR), or rest pressure (Pd/Pa)) as ground truth. Previous studies have shown that FFR computed from angiographic data (angioFFR) has slightly higher accuracy than FFR computed from coronary CT angiography data. As a result, angioFFR may also or instead be used as ground truth during the training. Alternatively, if the decision in the catheterization laboratory is not based on functional indices (measured or computed) and anatomical markers are used for decision making, these may be used during the training.

Once this database 30 is assembled, relevant features and the corresponding clinical decisions are extracted 36, 38 and used to train 40 one or more data-driven surrogate models using machine learning algorithms. During the training phase, more features may be available than during the online prediction phase. The features which are missing during the prediction phase may be estimated based on similar datasets in the training database, (e.g. by employing a separate machine learning algorithm specifically trained for this purpose) or by substitution of an average.

In the embodiment where the machine training is to predict a decision of whether to perform CT-FFR, the training may be based, in part, on a measure of utility. The utility may account for the expected amount of time before the CT-FFR results are available, as compared to the state of the patient. Especially in emergency settings (e.g. in the emergency room) or for unstable patients, the additional wait time required by CT-FFR may increase risks for the patient (e.g. prolonged ischemia). The training learns to recommend alternative tests (e.g. invasive FFR) regardless of the expected CT-FFR results (i.e., learns to use utility to predict the decision whether to use CT-FFR). The utility may be used for learning to predict other decisions.

Given the cost pressure in routine clinical workflows and the significant time and resources allocated to performing CT-FFR for a patient, cost effectiveness may also be used for training. A value or values represented cost effectiveness is used in training. Alternatively or additionally, the data used for training is limited to only features that are already available or may be determined at no cost or with very little additional cost.

One predictor may be trained to output multiple decisions. In case of more than two options, a multiple option choice may be performed (e.g. using a multi-class classifier). Alternatively, a cascade or parallel set of machine-learnt predictors are trained. The machine learning algorithms may be used in a cascaded or parallel workflow. Each predictor is trained to make one or more (a sub-set) of the possible decisions. Each decision may be followed by more fine-grade options of that decision by the same or a different predictor (e.g., if the decision is to send the patient to the catheterization laboratory for further investigations, the machine learning model may be further employed to decide which type of investigations should be performed in the catheterization laboratory (e.g., X-ray Angiography, optical coherence tomography (OCT), intravascular ultrasound (IVUS), or invasive FFR/IFR)). If the decision is to send the patient home, the machine learning model may be further employed to decide which type of medication should be prescribed and/or when should the patient return for a follow-up screening. The clinical decision may be a series of hierarchical decisions, such as: send the patient to the catheterization laboratory for further invasive testing and/or intervention (e.g. diagnostic catheterization, PCI, or CABG) or do not send the patient to the catheterization laboratory, but instead send the patient for another non-invasive test (e.g., perfusion imaging, SPECT, or stress echocardiography), or discharge the patient and prescribe medication, including what type of medicine.

Cascaded predictors may be employed to provide increasing levels of details for the clinical decision. A first predictor decides if further medical exams are required or not. A second predictor may decide which type of further medical exams are required. A third predictor may decide the specific acquisition parameters of the medical examination. Any cascade, hierarchal, and/or multi-class training and resulting predictors may be used.

Returning to the application of the machine-learnt predictor of FIG. 1 (online or application phase of machine learning), the machine-learnt predictor generates the clinical decision or decisions in response to input of the input vector. The decision is a recommendation for the treatment of the patient. Any clinical decisions may be made. In one embodiment, the treatment options include sending the patient for invasive stenting, sending the patient for invasive measurement, sending the patient for a non-invasive test, prescribing medication to the patient, and/or discharging the patient. Additional, different, or fewer options and corresponding decisions may be provided. For example, the decision is for what intervention and/or invasive testing to use (e.g., diagnostic catheterization, percutaneous coronary intervention (PCI), coronary artery bypass grafting (CABG), or stenting).

The decision may be to or not to perform further examination or testing. For example, decisions are provided for: Thallium stress test (i.e., myocardial perfusion imaging (MPI), multigated acquisition (MUGA) scan, radionuclide stress test, or nuclear stress test), exercise stress test (i.e., treadmill test, exercise test, or exercise cardiac stress test (ECST), cardiac CT (i.e., tomography, including CT, CAT scan, EBCT, DCA, DSA, multidetector CT (MDCT)), magnetic resonance imaging, myocardial perfusion scintigraphy using single photon emission computed tomography (SPECT) or positron emission tomography (PET), perfusion rest/stress CMR, electrocardiogram (EKG/ECG), stress or rest echocardiography, X-ray angiography, rotational angiography, OCT, IVUS, or invasive pressure, flow, or resistance measurements (e.g., FFR, IFR, CFR, BSR, rest Pd/Pa, HSR, hyperemic IFR, or IMR). Stress imaging may be performed either with exercise or pharmacologically. In general, exercise stress imaging is preferred over pharmacological testing if a patient can exercise to a sufficient cardiac workload because exercise can provide higher physiological stress and better correlation between a patient's symptoms and physical work capacity than what would be achieved by pharmacological testing. If stress is induced pharmacologically, the clinical decision may also refer to the vasodilating agent of choice (e.g., adenosine, dipyridamole, regadenoson, or dobutamine).

The clinical decision may be defined at patient level or at lesion or plaque level. The decision is for treatment of the patient and/or for treatment of specific lesions or plaques.

The clinical decision may be binary. For example, the decision is whether to send the patient to the catheterization laboratory. As another example, the decision is whether patient has no significant coronary artery disease or may have significant coronary artery disease (e.g., send patient home or not). In yet another example, the decision is whether CT-FFR will be negative at all locations or CT-FFR may be positive at certain locations (i.e., decision to or not to perform CT-FFR).

The machine-learnt predictor may produce results ("clinical decision") either as an absolute value (with probability=1) or as a set of probabilities for each decision. For example, the result may be as follows: send the patient to the catheterization laboratory-probability→0.95, and do not send the patient to the catheterization laboratory-probability→0.05. The clinical decision may be a continuous variable, like the settings or parameters of a future screening examination. The output from the predictor may also include a confidence score, along with potential sources of uncertainty. Missing data and the magnitude of the effect of the missing data on the decision may be indicated.

Besides the decision, the clinical decision support system may additionally indicate a decision motivation. The decision motivation embeds the patient-specific characteristics or features that are most important for the decision (e.g. calcium score >400, age >65→CT-FFR test not required since the probability for catheterization laboratory intervention is higher than 95%).

By using a machine-learnt predictor, data from heterogeneous sources may be integrated to perform a comprehensive assessment. The online prediction phase is, outputting results in near real-time (e.g., within a few seconds). As a result, the machine-learnt predictor may be run directly on a workstation on-site and be readily accessible to the clinician for assistance in decision making.

In one embodiment, the predictor determines whether to perform CT-FFR as the clinical decision. Where the predictor is machine trained, the machine-learnt predictor is based on training data with a ground truth from invasive FFR and/or angioFFR. Alternatively, CT-FFR is used as the ground truth.

The predictor may predict the values for CT-FFR without performing the CT-FFR, thus avoiding the input by a user or processor of segmentation of the arteries. The predictor predicts CT-FFR values as being either positive, negative or lying in a grey-zone (i.e., being within predefined values). In another embodiment, the predictor may predict bin-based CT-FFR values (e.g. each bin spanning an interval of 0.1 with the prediction being of a distribution of CT-FFR values for the locations in the patient). The predicted values may refer to the entire patient or to certain branches (main branches, side branches). The predictor may predict if CT-FFR is required for certain branches. As a result, the user may be able to focus on the selected branches while running the CT-FFR application, thus shortening the total runtime for the CT-FFR test.

In one example, the predictor determines merely that no CT-FFR is recommended for the patient. The decision may include other options, such as generating the clinical decision as invasive treatment of the patient or medicinal treatment without the CT-FFR. The decision is to skip performance of CT-FFR for the patient. In another example, the predictor determines merely that CT-FFR is recommended for the patient.

Figure 4:
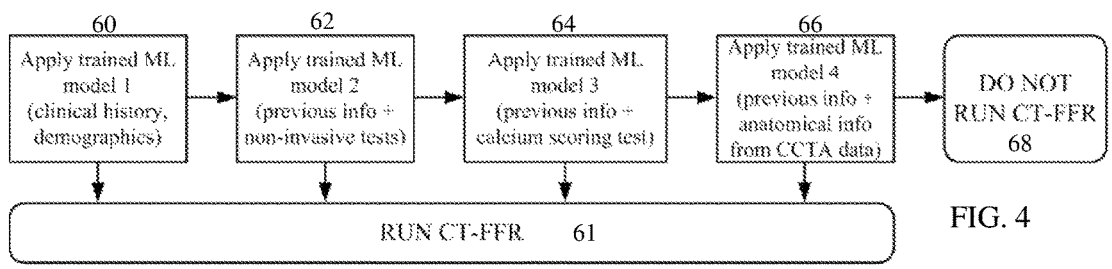
FIG. 4 illustrates an example cascade of machine-learnt predictors for CT-FFR decision.

FIG. 4 shows an example hierarchal arrangement of predictors for determining whether to perform 61 CT-FFR. As such, some of the features may be evaluated before performing the coronary CT angiography examination to acquire the CT data to be used by the CT-FFR algorithm. Each stage or predictor 60, 62, 64, 66 determines whether to perform 61 CT-FFR. The first predictor 60 operates on a reduced input vector, such as patient data not including than the coronary CT data and including clinical history and demographics. If the prediction is not to perform 61 CT-FFR, the decision is to gather additional information, such as non-invasive tests. The second predictor 62 operates on a larger input vector, such as including the previous information and results from non-invasive test or tests. The prediction is to perform 61 CT-FFR or to gather more data. If the prediction is not to perform 61, the decision is to perform a calcium scoring test. The third predictor 64 operates on the previous information from the second predictor plus results from the calcium scoring test. The prediction is to perform 61 or to gather more data in the form of the coronary CT angiography scan. The fourth predictor 66 uses the available information (previous information and the CT data) to recommend performance 61 or not to perform 68 the CT-FFR.

In another embodiment, the decision whether to perform CT-FFR occurs during performance of CT-FFR. The clinical decision becomes whether to cease performing CT-FFR before completion. The decision making occurs while running the CT-FFR. If the requirement for the CT-FFR test is not excluded a priori, a decision to stop running the CT-FFR test may be taken during the test (e.g. either because coronary artery disease can be excluded or because coronary artery disease is classified as being functionally significant and the patient needs to be sent to the catheterization laboratory). The machine-learnt predictor may be employed to take such a decision based on partial information as that information is acquired for the CT-FFR. For example, anatomical information extracted using fully automated centerline and segmentation algorithms is used. Anatomical information of main branches may be used. Any subset of the features that are generated during performance of the CT-FFR may be used with other patient information to make the decision whether to continue. Measures of uncertainty may be integrated for any type of the above listed features and information.

In act 22, the clinical decision is transmitted. The transmission is to a display, such as a monitor, workstation, printer, handheld, or computer. Alternatively or additionally, the transmission is to a memory, such as a database of patient records, or to a network, such as a computer network.

The transmission provides information for the physician decision. The clinical decision support system provides an initial or starting recommendation, which may be approved or disapproved by the treating physician. The radiologist may use the recommended decision or decisions to determine what measures to perform or how much time to spend on any measures. The physician accesses the recommended treatment from memory, such as the patient record, and/or from a display.

In one embodiment, the clinical decisions are visualized, either as text or in a graphical way (e.g. overlaid on the medical images), and presented to the clinician. Decision support information, such as treatments, risks, guidelines, or other information, may be output. Diagnostic rules for verifying the cause, such as based on guidelines or studies, may be output as decision support.

Clinical decisions may be visualized on the CT scanner or on another device, such as an imaging workstation. For example, the clinical decision support system provides a touch screen enabling interactions with this workflow (gestures to rotate, zoom, pan). Point and touch causes the system to display the value of interest at the point of touch.

The decisions may be presented with estimates of the evolution of the patient in time. For example, predictions of an amount of time to the next MACE, re-hospitalization, and/or death are provided with the decisions and/or with non-recommended decisions. The probability of no event occurring in a period may be predicted. As such, for a specific clinical decision, the likely evolution of the patient over a certain period may be displayed to the user, accompanied for example by a future screening date.

Figure 3:
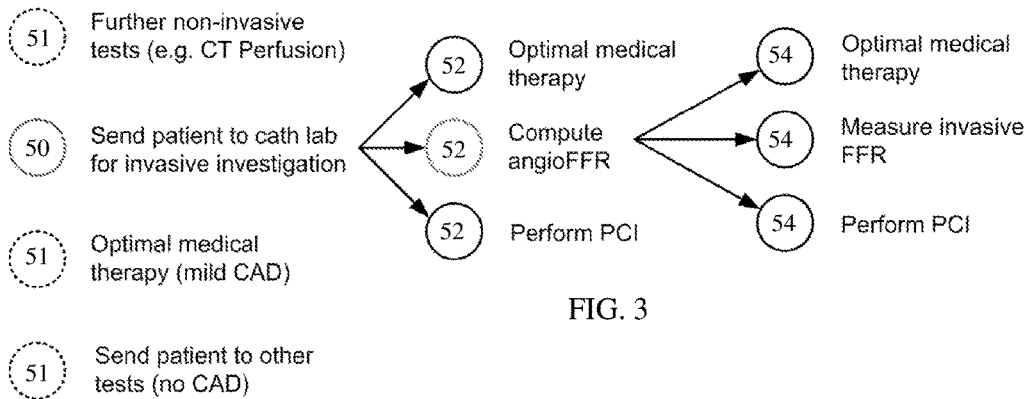
FIG. 3 illustrates an example visual output of coronary CT-based clinical decision support.

Any display of the decision or decisions may be used. In one embodiment, a decision tree shows the clinical decision, other possible decisions, and further treatment options resulting from the clinical decision. Besides a basic text based display, another option is to display in a hierarchy not only the currently selected clinical decision but also possible subsequent clinical decisions. FIG. 3 shows an example display. The recommended treatment or clinical decision 50 after the coronary CT scan is to send the patient to the catheterization laboratory for invasive investigation. As a result, various options 52, 54 at the time of the investigation in the catheterization laboratory are displayed. The options 51 not recommended may or may not be shown. Moreover, the user may be able to select one of the options 52 for the subsequent stages and, as a result, the viable clinical decisions 54 at the next stage may be displayed. Alternatively or additionally, the clinical decision support system recommends the subsequent decision at each stage. Other visualizations may be used.

The decision support system is implemented locally. One advantage of a machine-learnt predictor is that the online prediction is fast, outputting results almost instantaneously or in a matter of seconds given access to the information. Hence, the machine-learnt predictor may be run directly on the workstation located at a clinic or hospital. The system may be run on a portable device (e.g., an instance of wearable computing). The system may be combined with a personal assistant interacting with the individual in natural language.

Alternatively, the decision support system may be available as a service and/or operated remotely. A server or other remote processor is accessed by the hospital or clinician to obtain the patient-specific clinical decision. A hybrid on-site/off-site processing workflow may be used. Off-site processing may provide more detailed information or additional information than would be available on-site, which is enabled by the less strict requirement on the processing time. Examples of such scenarios include employing a complex computational model available off-site but not on-site for providing further input information or features. On-site assessment may not be available at the time when the medical images are acquired. This may be due for instance to limitations of the imaging workstation (e.g., incompatible hardware or software configuration) or unavailability of the workstation providing the processing functionality. In this case, off-site processing may be offered as an alternative to produce the same results as the on-site counterpart or with the possibility of choosing different options. The on-site assessment may be inconclusive or uncertain due to limitations of the predictor (e.g. the data set being processed has features outside the range considered in the training set). In this case, the off-site processing may include re-training the machine-learnt predictor so that the feature values of the new case are within those of the training dataset. The on-site assessment may be inconclusive or uncertain due to intrinsic uncertainty of clinical decisions. In this case, off-site processing may include consulting medical experts (human or databases) to find the best course of action, for instance based on previous clinical cases with similar characteristics.

If the predicted decision is to perform another medical examination (imaging or non-imaging), the clinical decision support system may be used to schedule the examination in the hospital. Such information may be used to perform an optimized scheduling of patients for medical exams. Multiple parallel machine-learnt models may be employed for this purpose.

The predictor is trained for general use at different facilities. Alternatively, each clinical center, institution, hospital network, or medical practice defines their own clinical decisions (e.g., based on the available medical devices, scanners and/or examinations). The predictor for clinical decision making may be adapted for the specific setting or availability to avoid recommending unavailable decisions if there is an available alternative. The machine-learnt predictor may be trained centrally (using all available datasets) or using only the datasets from a specific hospital.

FIG. 5 shows a system for coronary decision support, such as a system for FFR decision support or other coronary CT clinical decision support. The system implements the method of FIG. 1 or another method to output recommended clinical decisions, such as shown in FIG. 3. Coronary CT data and other patient information are used to recommend clinical decisions.

The system includes a CT scanner 80, a decision support processor 82, a memory 84, a graphical user interface (GUI) 88 with a user input 85 and a display 86, and one or more machine-learnt classifiers 90. Additional, different, or fewer components may be provided. For example, a network or network connection is provided, such as for networking with a medical imaging network or data archival system or networking between the CT scanner 80 and the decision support processor 82. In another example, the user input 85 is not provided. As another example, a server is provided for implementing the decision support processor 82 and/or machine-learnt classifiers 90 remotely from the CT scanner 80.

The decision support processor 82, memory 84, user input 85, display 86, and/or machine learnt classifiers 90 are part of the CT scanner 80. Alternatively, the decision support processor 82, memory 84, user input 85, display 86, and/or machine learnt classifiers 90 are part of an archival and/or image processing system, such as associated with a medical records database workstation or server, separate from the CT scanner 80. In other embodiments, the decision support processor 82, memory 84, user input 85, display 86, and/or machine learnt classifiers 90 are a personal computer, such as desktop or laptop, a workstation, a server, a network, or combinations thereof.

The CT scanner 80 is a medical diagnostic imaging CT system. A gantry supports a source of x-rays and a detector on opposite sides of a patient examination space. The gantry moves the source and detector about the patient to perform a coronary CT angiography scan. Various x-ray projections are acquired by the detector from different positions relative to the patient. Computed tomography solves for the two or three-dimensional distribution of the response from the projections. Ultrasound, x-ray, fluoroscopy, positron emission tomography, single photon emission computed tomography, and/or magnetic resonance systems may additionally be used.

The memory 84 may be a graphics processing memory, a video random access memory, a random access memory, system memory, cache memory, hard drive, optical media, magnetic media, flash drive, buffer, database, combinations thereof, or other now known or later developed memory device for storing data. The memory 84 is part of the CT scanner 80, part of a computer associated with the decision support processor 82, part of a database, part of another system, a picture archival memory, or a standalone device.

The memory 84 stores patient data, such as in a computerized patient record. Any of the patient data discussed herein may be stored, such as coronary CT data, fit models, parameters from fit models, measurements, clinical data, non-invasive test results, and/or biochemical measurements. The memory 84 alternatively or additionally stores a matrix or matrices embodying one or more machine-learnt predictors. Rule-based or other predictors may be stored. The memory 84 may alternatively or additionally store data during processing, such as storing information discussed herein or links thereto.

The memory 84 or other memory is alternatively or additionally a non-transitory computer readable storage medium storing data representing instructions executable by the programmed decision support processor 82 or a processor implementing the clinical decision support and/or machine-learnt classifiers 90. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The decision support processor 82 is a general processor, central processing unit, control processor, graphics processor, digital signal processor, three-dimensional rendering processor, application specific integrated circuit, field programmable gate array, digital circuit, analog circuit, combinations thereof, or other now known or later developed device for applying a clinical decision predictor. The decision support processor 82 is a single device or multiple devices operating in serial, parallel, or separately. The decision support processor 82 may be a main processor of a computer, such as a laptop or desktop computer, or may be a processor for handling some tasks in a larger system, such as in the CT scanner 80. The decision support processor 82 is configured by instructions, design, hardware, and/or software to perform the acts discussed herein.

The decision support processor 82 is configured to acquire and/or extract an input feature vector from the coronary CT data and the computerized patient record. For example, the input feature vector includes values from non-invasive patient data and biochemical measurements from the computerized patient record, and the input feature vector includes values for features from the coronary CT data, anatomical information derived from the coronary CT data, and/or functional evaluation value derived from the coronary CT data.

The decision support processor 82 is configured to apply the input feature vector to a machine-learnt classifier. The decision support processor 82 may be configured to calculate values for features and input the values to a machine-learnt classifier 90 to predict one or more clinical decisions for a specific patient.

The machine-learnt classifiers 90 are implemented by the decision support processor 82 or other processor with access to the matrices defining the classifiers 90 stored in the memory 84 or other memory. The machine-learnt classifiers 90 are matrices of inputs (i.e., values of features in the input vector), weights, relationships between weighted inputs or other layers, and outputs of recommended decisions, probability of correctness for the recommended decisions, utility of the decisions, and/or cost of the decisions.

Any machine training may be used to create the machine-learnt classifiers 90. For example, a support vector machine is used. As another example, deep learning is used to both train the classifier and learn distinguishing features (e.g., learn convolution or filter kernels to extract determinative information from the scan and/or patient data). The machine-learnt classifiers 90 are trained to relate input values to decisions. The probability of any given decision being correct or matching the knowledge incorporated into the machine-learnt predictor may be estimated.

One or more machine-learnt classifiers 90 are provided. For example, one machine-learnt classifier 90 is provided for each of multiple possible decisions in treating coronary artery disease. Cascade, parallel, or multi-class classifiers may be used. In one embodiment, a single classifier is provided for a single decision, such as one classifier 90 to determine whether to perform CT-FFR.

The decision support processor 82, using the machine-learnt classifier 90, is configured to output a clinical decision for the patient in response to the application of the input feature vector. The output of the clinical decision may be prior to entry of a treatment into the computerized patient record by a physician. The recommended decision helps guide the treating physician, so is provided to the treating physician prior to entry of an order for the patient. Alternatively, the output decision is used as the order without the intervening physician. The output decision may be provided prior to review of the coronary CT data by a radiologist. Other timing may be provided.

In the embodiment where the machine-learnt classifier 90 is configured by training to output a decision of whether to perform CT-FFR, the output is prior to entry of an instruction about CT-FFR into the computerized patient record for the patient by a physician. Where the recommendation is not to perform the CT-FFR, the cost and time associated with CT-FFR may be avoided. The decision may be due to the patient having or not likely having coronary artery disease based on the machine-learnt association of the input feature vector to the decision. A hierarchy of machine-learnt classifiers 90 may be used for the decision. The machine-learnt classifier 90 for determining whether to perform CT-FFR may be applied during performance of CT-FFR. If sufficient determinative information results from partial application of CT-FFR, then the decision may be to cease further performance to save time or money.

The decision support processor 82 may be configured to generate a graphic user interface (GUI) 88 for input of values or data and/or for outputting decisions. The GUI 88 includes one or both of the user input 85 and the display 86.

The GUI 88 provides for user interaction with the decision support processor 82, CT scanner 80, and/or machine-learnt classifiers 90. The interaction is for inputting information (e.g., selecting patient files) and/or for reviewing output information (e.g., viewing recommended decisions with or without supporting information such as probabilities and/or values of features input to the classifier 90). The GUI 88 is configured (e.g., by loading an image into a display plane memory) to display the decision or decisions.

The user input device 85 is a keyboard, mouse, trackball, touch pad, buttons, sliders, combinations thereof, or other input device. The user input 85 may be a touch screen of the display 86. User interaction is received by the user input device 85, such as a designation of a region of tissue (e.g., a click or click and drag to place a region of interest). Other user interaction may be received, such as for activating the classification.

The display 86 is a monitor, LCD, projector, plasma display, CRT, printer, or other now known or later developed devise for outputting visual information. The display 86 receives images of graphics, text, quantities, spatial distribution of anatomy or function, or other information from the decision support processor 82, memory 84, CT scanner 80, or machine-learnt classifiers 90.

One or more images are displayed. The images may or may not include anatomical representation or imaging, such as an anatomical image from the coronary CT data. The image includes one or more recommended decisions, such as an annotation on a CT image or in a display of a report for the patient. Indications of probability may be included in the image. The image includes an indication, such as a text, a graphic, or colorization, of the classification of the patient for the decision. In one embodiment, a decision tree with one or more recommended decisions and possible alternative decisions is displayed, such as shown in FIG. 3. Instead of outputting one specific decision, the machine-learnt classifier 90 may be used to present to the user the top n (e.g. 3) possible decisions, ranked based on their corresponding confidence. The user may then select the final decision.

The clinical decision support system is fully automated. The recommended decisions are output once activated with no more input other than the activation. Other inputs, such as to select information or configure the system, may be used. In an alternative embodiment, the user or clinician intervenes, leading to semi-automated decision making. For example, the clinician may select a subset of decisions that are viable or seem appropriate (e.g., a certain type of invasive test may not be available in the hospital) from a large set of possible decisions. Hence, the decision support system outputs a decision from the sub-set of available decisions. Multiple machine-learnt classifiers may be trained for different subsets of possible decisions, or the same machine-learnt classifier may be employed irrespective of the selected viable decisions. The decision with highest probability from the selected set of available decisions may be suggested. The clinician may intervene in the workflow by choosing to discard some of the input information or features that are considered irrelevant.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for coronary decision support using a computed tomography (CT)-based clinical decision support system, the method comprising:
    scanning a patient with a computed tomography system, the scanning providing coronary CT data representing a heart of the patient;
    acquiring, from a computerized medical record database, patient data different than the coronary CT data;
    extracting values for features of an input vector of a machine-learnt predictor of the CT-based clinical decision support system from the coronary CT data and the patient data;
    generating, by the machine-learnt predictor of the CT-based clinical decision support system, a clinical decision for treatment of the patient based on the input vector; and
    transmitting the clinical decision.

2. The method of claim 1 wherein acquiring, extracting, generating, and transmitting are performed upon scanning and before a review by a physician.

3. The method of claim 1 wherein acquiring comprises acquiring as the patient data (1) a CT-based fractional flow reserve (FFR) value and (2) clinical data for the patient, and not acquiring an invasive FFR prior to performing the generating, and wherein extracting comprises extracting the values from the CT-FFR value and the clinical data.

4. The method of claim 1 wherein generating comprises determining whether to perform CT-based fractional flow reserve (FFR) as the clinical decision.

5. The method of claim 1 wherein acquiring comprises acquiring non-invasive data, biochemical information, and model information fit to the coronary CT data, and wherein extracting comprises extracting the values from the CT-FFR value, the clinical data, the model information, and the coronary CT data.

6. The method of claim 1 wherein acquiring comprises acquiring model information fit to the coronary CT data, the model information being from a physiological or functional model, from an anatomical model, or from both the physiological or functional model and the anatomical model, and wherein extracting comprises extracting the values from the model information, and the coronary CT data.

7. The method of claim 1 wherein generating comprises generating the clinical decision from options including sending the patient for invasive stenting, sending the patient for invasive measurement, sending the patient for a non-invasive test, prescribing medication to the patient, and discharging the patient.

8. The method of claim 1 wherein generating comprises generating the clinical decision as a recommendation for the treatment.

9. The method of claim 1 wherein generating comprises generating with the machine-learnt predictor comprising a cascade or parallel set of machine-learnt classifiers.

10. The method of claim 1 wherein transmitting comprises transmitting the clinical decision as information for physician decision.

11. The method of claim 1 wherein transmitting comprises displaying a decision tree showing the clinical decision, other possible decisions, and further treatment options resulting from the clinical decision.

12. A system for coronary decision support, the system comprising:
    a computed tomography (CT) scanner for scanning a patient, the CT scanner is configured to output coronary CT data for the patient;
    a memory stores a computerized patient record; and
    a decision support processor configured to extract an input feature vector from the coronary CT data and the computerized patient record, to apply the input feature vector to a machine-learnt classifier, and to output a clinical decision for the patient from the machine-learnt classifier in response to the application of the input feature vector.

13. The system of claim 12 wherein the decision support processor is configured to output the clinical decision prior to entry of a treatment into the computerized patient record by a physician.

14. The system of claim 12 wherein the decision support processor is configured to output the clinical decision prior to review of the coronary CT data by a radiologist.

15. The system of claim 12 wherein the clinical decision comprises a recommendation to perform non-invasive CT-based fractional flow reserve.

16. The system of claim 12 wherein the input feature vector comprises non-invasive patient data and biochemical measurements from the computerized patient record and comprises features from the coronary CT data, anatomical information derived from the coronary CT data, and functional evaluation value derived from the coronary CT data.

17. The system of claim 12 further comprising a display configured to display the clinical decision in a decision tree of possible clinical decisions.

* * * * *